US011712152B2

(12) United States Patent
Iyoshi et al.

(10) Patent No.: US 11,712,152 B2
(45) Date of Patent: Aug. 1, 2023

(54) ENDOSCOPE AND INSERTION SECTION OF ENDOSCOPE HAVING FIRST AND SECOND RESINS FOR RETAINING OPTICAL MEMBER AT DISTAL END

(71) Applicant: OLYMPUS CORPORATION, Tokyo (JP)

(72) Inventors: Eita Iyoshi, Hachioji (JP); Yoshimi Konno, Hachioji (JP); Hiroaki Kinoshita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 366 days.

(21) Appl. No.: 17/102,918

(22) Filed: Nov. 24, 2020

(65) Prior Publication Data
US 2021/0093164 A1    Apr. 1, 2021

Related U.S. Application Data

(63) Continuation of application No. PCT/JP2019/006316, filed on Feb. 20, 2019.

(30) Foreign Application Priority Data

May 31, 2018   (JP) .................... 2018-105111

(51) Int. Cl.
*A61B 1/00*        (2006.01)
*A61B 1/05*        (2006.01)

(52) U.S. Cl.
CPC .......... *A61B 1/00096* (2013.01); *A61B 1/051* (2013.01); *A61B 1/00163* (2013.01)

(58) Field of Classification Search
CPC ..................... G02B 23/2423; G02B 23/243
See application file for complete search history.

(56) References Cited

U.S. PATENT DOCUMENTS 5,894,369 A * 4/1999 Akiba ................ G02B 23/2423
                                                       600/110
2009/0093681 A1* 4/2009 Ichimura .............. A61B 1/0623
                                                       600/178
(Continued)

FOREIGN PATENT DOCUMENTS

JP         09-234183 A      9/1997
JP      2006-239185 A       9/2006
(Continued)

OTHER PUBLICATIONS

International Search Report dated May 7, 2019 received in PCT/JP2019/006316.

*Primary Examiner* — John P Leubecker
(74) *Attorney, Agent, or Firm* — Scully, Scott, Murphy & Presser, P.C.

(57) ABSTRACT

An endoscope includes: a barrel having an opening of a through hole on an outer surface; a lens inserted into the through hole and having a distal end surface which protrudes from the outer surface; a first resin disposed between a wall surface of the through hole and a side surface of the lens; and a second resin disposed on a surface of the first resin, a portion of the barrel disposed around the opening, and an entire circumference of an outer peripheral portion of the distal end surface of the lens, the second resin forming a protruding portion which protrudes from the distal end surface of the optical member, containing light blocking particles, and having a larger fracture toughness value than the first resin.

20 Claims, 5 Drawing Sheets

(56) References Cited

U.S. PATENT DOCUMENTS

| | | | | |
|---|---|---|---|---|
| 2009/0244727 A1* | 10/2009 | Ishii | ............ | A61B 1/00165 |
| | | | | 359/819 |
| 2010/0022841 A1* | 1/2010 | Takahashi | ............ | A61B 1/127 |
| | | | | 600/162 |
| 2014/0058201 A1* | 2/2014 | Mizuyoshi | ............ | G02B 23/26 |
| | | | | 600/129 |
| 2014/0275786 A1* | 9/2014 | Goto | ............ | G02B 23/243 |
| | | | | 600/133 |

FOREIGN PATENT DOCUMENTS

| | | | |
|---|---|---|---|
| JP | 2008-200158 A | | 9/2008 |
| JP | 2013-013712 A | | 1/2013 |
| JP | 2013233257 A | * | 11/2013 |

\* cited by examiner

ENDOSCOPE AND INSERTION SECTION OF ENDOSCOPE HAVING FIRST AND SECOND RESINS FOR RETAINING OPTICAL MEMBER AT DISTAL END

CROSS REFERENCE TO RELATED APPLICATION

This application is a continuation application of PCT/JP2019/006316 filed on Feb. 20, 2019 and claims benefit of Japanese Application No. 2018-105111 filed in Japan on May 31, 2018, the entire contents of which are incorporated herein by this reference.

BACKGROUND OF THE INVENTION

1. Field of the Invention

The present invention relates to an endoscope where an optical member is fixed to a barrel disposed on a distal end portion of an insertion section by a resin, and an insertion section of the endoscope.

2. Description of the Related Art

A type of endoscope has been popularly used where an elongated insertion section is inserted into the inside of a body of a subject which cannot be observed from the outside, the inside of the body is observed by an image pickup unit disposed on the distal end portion, and treatment is performed using a treatment instrument protruded from the distal end portion. After the endoscope is used, to prevent infection between patients, reprocess treatment including cleaning, disinfecting and sterilization is performed.

In Japanese Patent Application Laid-Open Publication No. 2013-13712, an endoscope is disclosed where a lens 133 of an illumination optical system and a cover glass 135 of an image pickup optical system, that is, optical members are fixed to a distal end 131 of an insertion section by an adhesive agent 137, and an annular protruding portion 139 is disposed on an outer peripheral edge of the optical member for preventing flare. An epoxy adhesive or a silicon adhesive is used as the adhesive agent 137, and blackened epoxy adhesive is used for forming the protruding portion 139.

SUMMARY OF THE INVENTION

An endoscope of an embodiment includes: a barrel disposed on a distal end portion of an insertion section and having an opening of a through hole in an outer surface; an optical member inserted into the through hole and having a distal end surface which is disposed in a protruding manner from the outer surface; a first resin disposed between a wall surface of the through hole and a side surface of the optical member; and a second resin disposed on a surface of the first resin, a portion of the barrel disposed around the opening, and an entire circumference of an outer peripheral portion of the distal end surface of the optical member, the second resin forming a protruding portion which protrudes from the distal end surface of the optical member, containing light blocking particles, and having a larger fracture toughness value than the first resin.

An insertion section of an endoscope of another embodiment includes: a barrel disposed on a distal end portion of the insertion section and having an opening of a through hole in an outer surface; an optical member inserted into the through hole and having a distal end surface which is disposed in a protruding manner from the outer surface; a first resin disposed between a wall surface of the through hole and a side surface of the optical member; and a second resin disposed on a surface of the first resin, a portion of the barrel disposed around the opening, and an entire circumference of an outer peripheral portion of the distal end surface of the optical member, the second resin forming a protruding portion which protrudes from the distal end surface of the optical member, containing light blocking particles, and having a larger fracture toughness value than the first resin.

DETAILED DESCRIPTION OF THE PREFERRED EMBODIMENTS

First Embodiment

Figure 1:
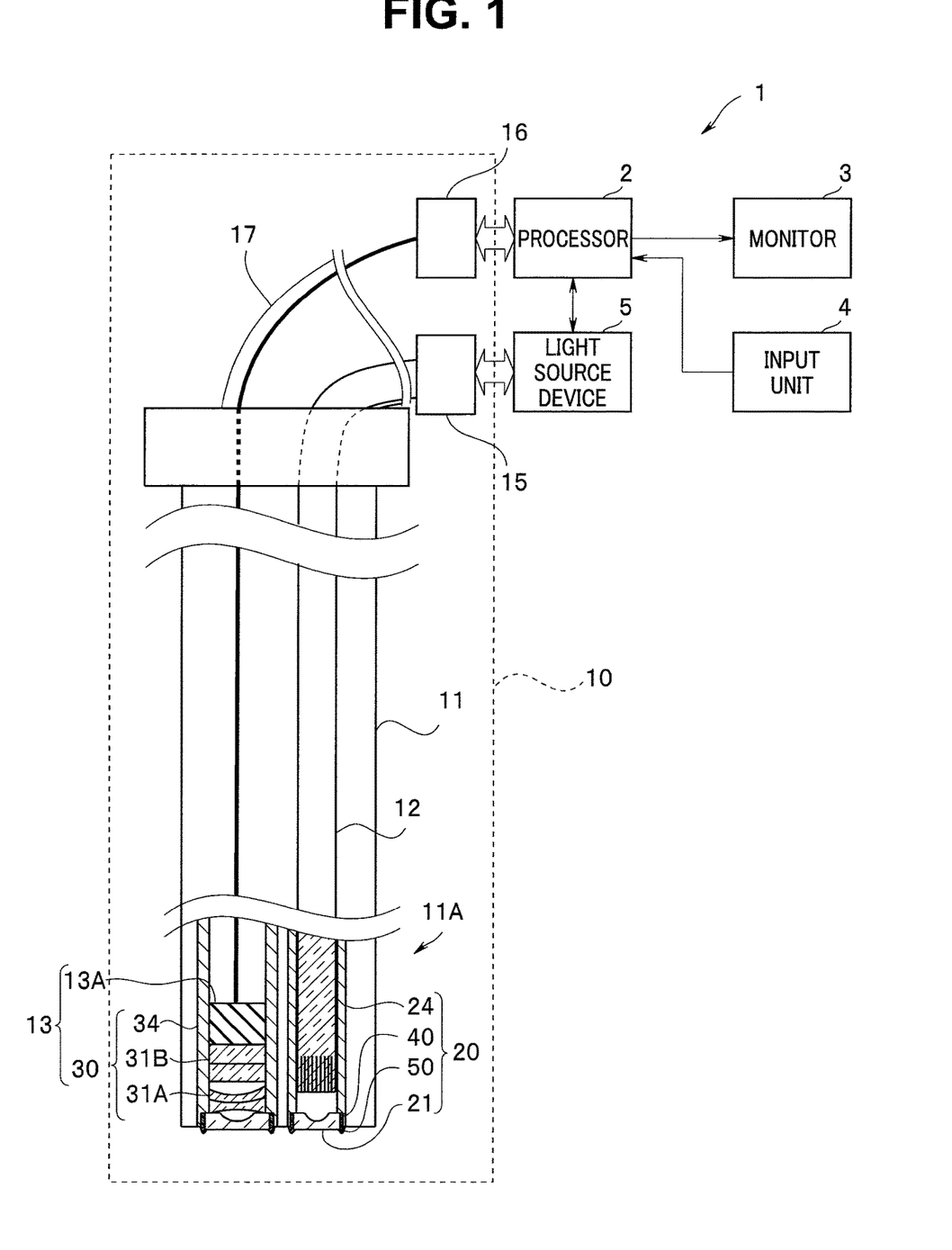
FIG. 1 is a configurational view of an endoscope system including an endoscope of a first embodiment.

As shown in FIG. 1, an endoscope 10 of the embodiment forms an endoscope system 1 together with a processor 2 which processes an image signal, a monitor 3, an input unit 4 for setting a use condition and the like, and a light source device 5.

In a description made hereinafter, drawings based on respective embodiments are schematic views. Accordingly, it must be noted that a relationship between a thickness and a width of each portion, a ratio between thicknesses, relative angles and the like of respective portions differ from the corresponding relationships of portions of an actual endoscope system. There may be a case where portions of the endoscope system are described with different size relationship or different ratios between the drawings. Illustration of some components and the indication of components by symbols may be omitted. An object direction is set as a frontward direction.

The endoscope 10 is a so-called flexible endoscope which includes: an elongated flexible insertion section 11 which is inserted into the inside of a body; and a universal cord 17 which extends from the insertion section 11 via an operation section (not shown). The insertion section 11 through which a light guide 12 passes has an image pickup unit 13 on a distal end portion 11A of the insertion section 11. The image pickup unit 13 includes: an image pickup optical unit 30 (hereinafter referred to as "optical unit 30"); and an image pickup device 13A such as a CCD. The universal cord 17 includes a light guide connector 15 connected to the light source device 5 and an electronic connector 16 connected to the processor 2 on a proximal end portion side.

A light which the light source device 5 generates is guided to the distal end portion 11A via the light guide connector 15 and the light guide 12, and is irradiated toward an object as an illumination light by an irradiation optical unit 20 (hereinafter referred to as "optical unit 20"). The illumination light is reflected on a surface of the object, and a reflection light of the illumination light is converged on an image pickup device 13A by the optical unit 30, and is picked up as an object image. Signal processing is applied to the image by the processor 2, and a processed image is displayed on a screen of the monitor 3. A wiring board on which an electronic component which applies primary processing to the image pickup signal is disposed may be bonded to the image pickup device 13A.

On a frontmost surface of the distal end portion 11A, a lens 21 which is an optical member of the optical unit 20, and a lens 31 which is an optical member of the optical unit 30 are disposed.

The optical unit 20 includes: the lens 21; and a lens barrel 24 which is a barrel for holding the lens 21. The optical unit 30 includes: lenses 31, 31A, 31B; and a lens barrel 34 which is a barrel for holding the lens 31 and the like.

Kinds, thicknesses, the number and a stacking order of a plurality of optical members can be suitably changed. In the endoscope 10, the lens barrel 24 of the optical unit 20 and the lens barrel 34 of the optical unit 30 are provided as separate bodies. However, the lens 21 and the lens 31 may be fixedly mounted on the same lens barrel.

The lens 21 and the like are transparent optical members made of glass, quarts, sapphire, stabilized zirconia (YSZ), yttrium-aluminum-garnet (YAG) or the like.

The lens 21 is a planoconcave lens having a negative power for irradiating an illumination light in a wide range. The lens 31 is also a planoconcave lens having a negative power for obtaining a wide field of view. However, the lenses 21 and 31 may be formed of a planoconvex lens depending on the configurations of the optical units 20 and 30. Front surfaces of the lenses 21 and 31 which form frontmost surfaces of the optical units 20 and 30 may preferably be formed of a flat surface for prevention of adhesion of a foreign substance and prevention of fracture caused by a shock.

In a case where a cover glass of a parallel flat plate is disposed on the frontmost portion of the optical unit, the optical member which is exposed on the frontmost surface of the distal end portion 11A is not the lens but is the cover glass of the flat plate.

As described later, for example, the lens 21 of the optical unit 20 is fixed to the lens barrel 24 by a first resin 40, and a surface of the first resin 40 is covered by a second resin 50 which forms a ring-shaped protruding portion.
<Configuration of Optical Unit>

Next, the configuration of the optical unit is described by taking the irradiation optical unit 20 as an example.

Figure 2:
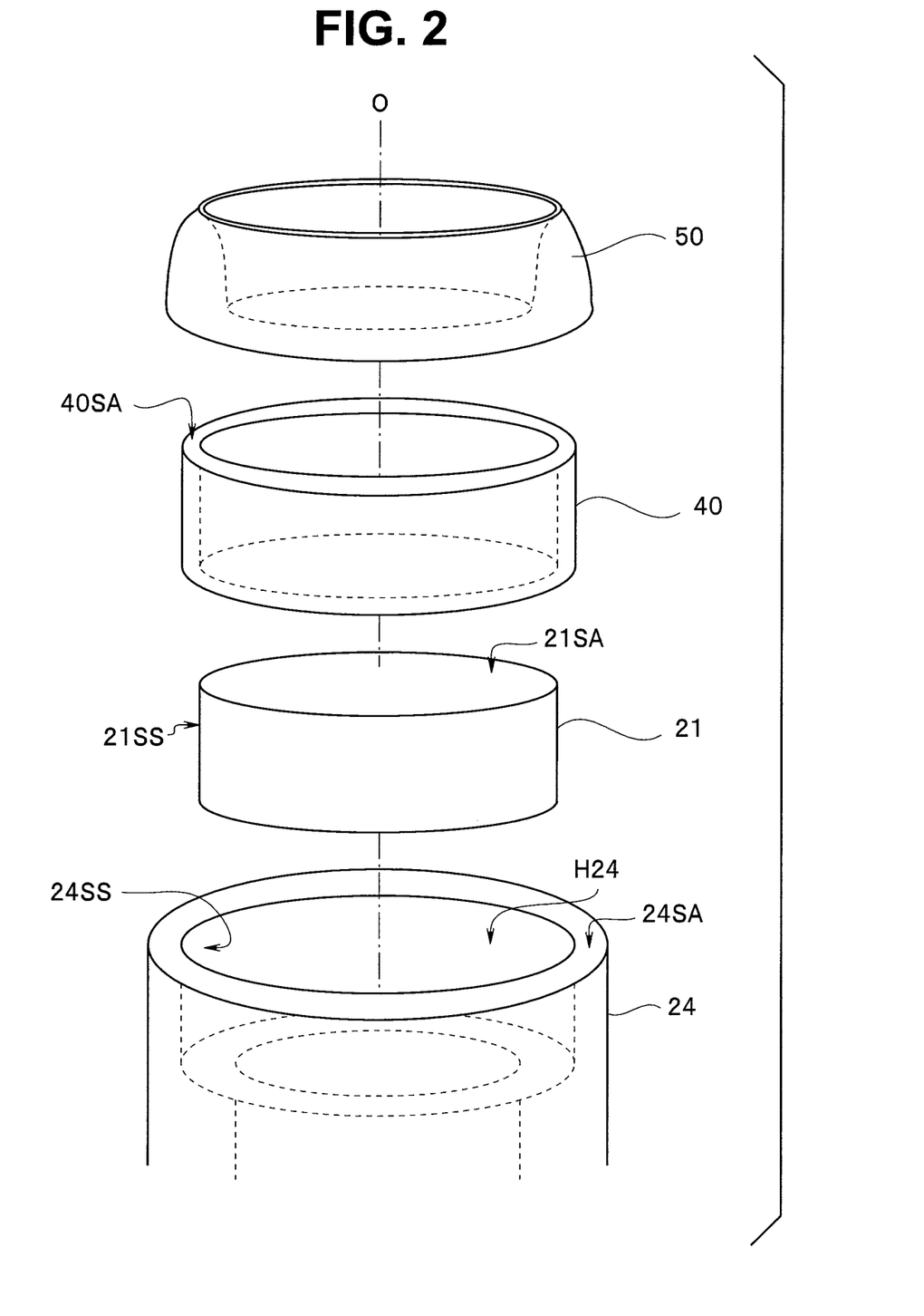
FIG. 2 is a perspective exploded view of an irradiation optical unit of the endoscope of the first embodiment.
Figure 3:
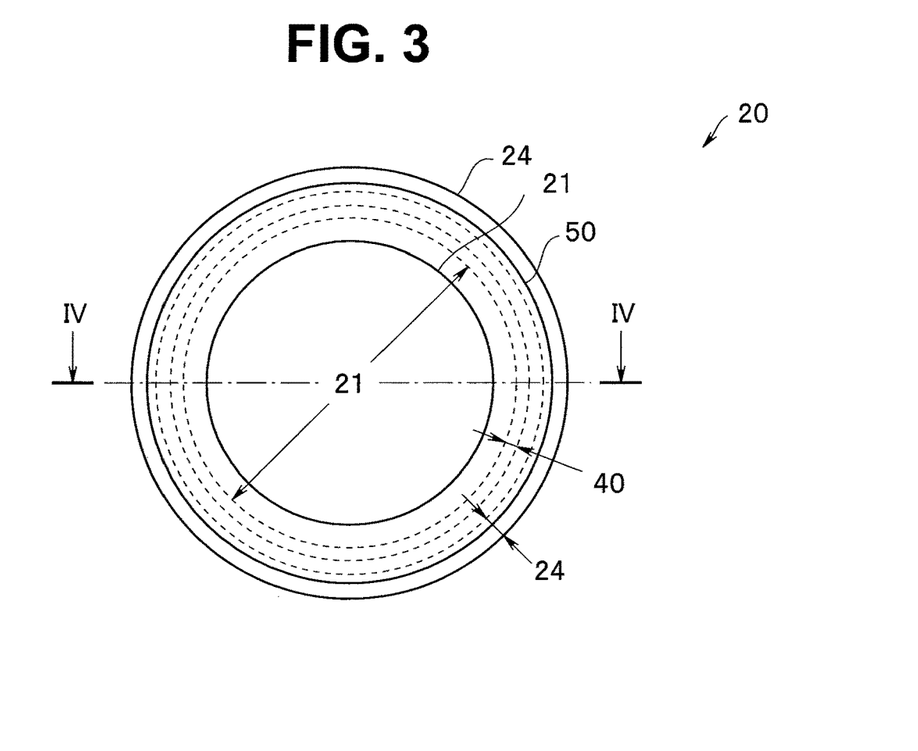
FIG. 3 is a plan view of a frontmost surface of the irradiation optical unit of the endoscope of the first embodiment.
Figure 4:
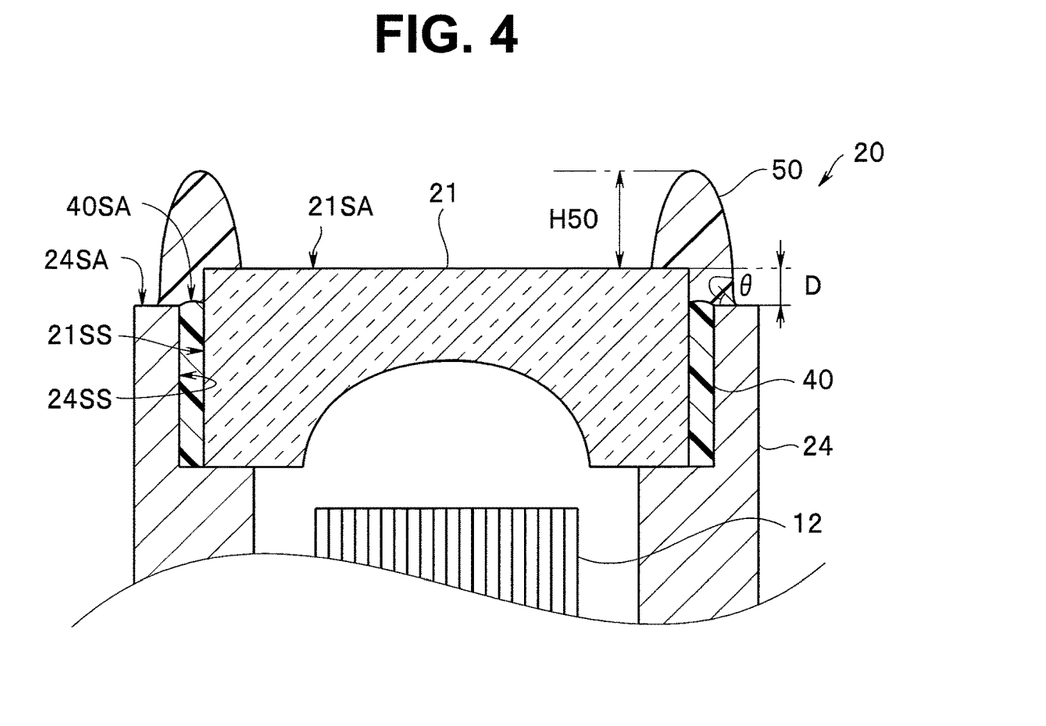
FIG. 4 is a cross-sectional view of the irradiation optical unit of the endoscope of the first embodiment taken along a line IV-IV in FIG. 3.

As shown in FIG. 2 to FIG. 4, the lens barrel 24 of the optical unit 20 is disposed on the distal end portion 11A of the insertion section 11. The lens barrel 24 has an opening of a through hole H24 in an outer surface 24SA. The outer surface 24SA is a front surface which is disposed closest to an object, and exposed to an outside. The lens barrel 24 is made of metal, for example, stainless steel. The lens 21 is inserted into the through hole H24 of the lens barrel 24, and a distal end surface 21SA of the lens 21 is disposed in a protruding manner from the outer surface 24SA of the lens barrel 24.

A protruding amount D of the distal end surface 21SA from the outer surface 24SA may preferably be 10 µm or more and 150 µm or less. When the protruding amount D is less than such a range or does not protrude from the outer surface 24SA, a foreign substance is liable to adhere to an outer periphery of the distal end surface 21SA, and the removal of such a foreign substance is not easy. When the protruding amount D exceeds such a range, the second resin 50 described later cannot be easily disposed, and a stepped portion cannot be easily eliminated even when the second resin 50 is disposed.

The first resin 40 is disposed between a wall surface 24SS of the through hole H24 and a side surface 21SS of the lens 21. The first resin 40 is an adhesive agent which fixes the lens 21 to the lens barrel 24.

The optical unit 20 includes the second resin 50 which forms a ring-shaped protruding portion, and covers the surface 40SA of the first resin 40, that is, the surface 40SA which is not brought into contact with the wall surface 24SS or the side surface 21SS. To completely cover the surface 40SA of the first resin 40, the second resin 50 is disposed also on a portion of the lens barrel 24 around an opening of the through hole H24 and on an entire circumference of an outer peripheral portion (outer peripheral edge) of the distal end surface 21SA of the lens 21.

Although the distal end surface 21SA protrudes from the outer surface 24SA, the stepped portion is covered by the second resin 50. Accordingly, the endoscope 10 possesses a favorable optical characteristic, and cleaning and the like of the endoscope 10 can be performed easily.

In the endoscope 10, the first resin 40 is a thermo-setting epoxy resin (Vickers hardness: Hv40=110, Young's modulus: E=5 GPa, fracture toughness value: K=0.4 MPa·m$^{1/2}$). The second resin 50 is a fiber-reinforced resin (fracture toughness value: K=2.5 MPa·m$^{1/2}$) which is formed by using a resin for forming the first resin 40 as a base material, and contains 5w % of short carbon fibers having a diameter of 0.1 µm.

The first resin 40 may preferably be a hard material for firmly fixing the lens 21 to the lens barrel 24. The first resin 40 may preferably have Vickers hardness Hv40 of 40 or more, and may more preferably have Vickers hardness Hv40 of 100 or more, for example. The first resin 40 may preferably have Young's modulus E40 of 2 GPa or more, and may more preferably have Young's modulus E40 of 4 GPa or more, for example. In a case where hardness Hv40 and Young's modulus E40 are less than the above-mentioned ranges, there is a concern that when the lens 21 receives a shock from an outside, the lens 21 moves in the through hole H24 of the lens barrel 24 and hence, an optical characteristic is deteriorated. Although an upper limit of hardness Hv40 and an upper limit of Young's modulus E40 are not particularly limited, the upper limit of hardness Hv40 is 250 and the upper limit of Young's modulus E40 is 10 GPa, for example.

Hardness Hv is measured based on an impression which is formed on a specimen when an indenter is inserted by pressing into the specimen under a condition of 25° C., a load of 1 kg and a pushing time of 15 seconds using a Vickers hardness meter in accordance with JIS Z2244. Young's modulus E40 is measured by performing a tensile test of a resin having a predetermined measurement shape.

The first resin 40 may preferably be a thermo-setting resin, and is an epoxy resin, a polystyrene resin, a melamine resin or the like. Among these resins, the thermo-setting epoxy resin is particularly preferable as the first resin 40 since the thermo-setting epoxy resin has a large Vickers hardness Hv40 so that the thermo-setting epoxy resin exhibits a strong adhering strength with the lens barrel 24.

On the other hand, the second resin 50 does not fracture even when the second resin 50 receives a shock from an outside and hence, the second resin 50 has a large fracture toughness value K (hereinafter referred to as "toughness value K").

Figure 5:
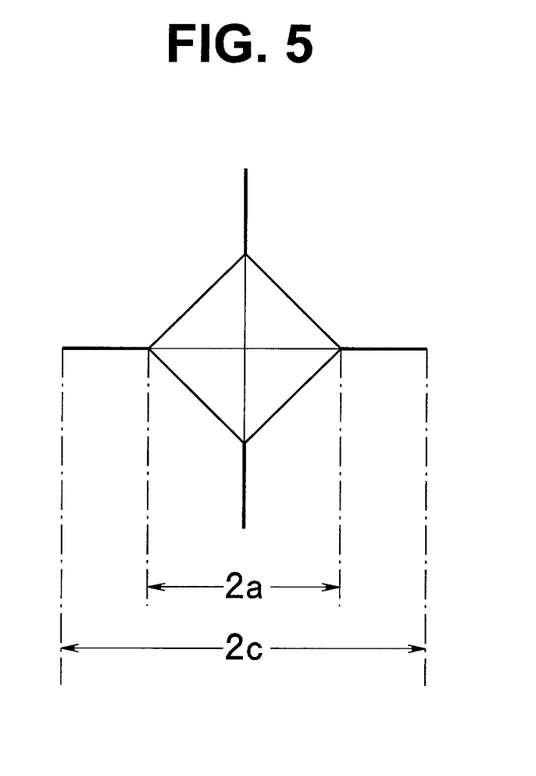
FIG. 5 is a schematic view of a Vickers impression having a crack.

The toughness value K is measured using an Indentation Fracture method (IF method). For example, a crack length c of an impression where the Vickers hardness Hv is measured in accordance with JIS (Japanese Industrial Standard) R1607 (Testing methods for fracture toughness of fine ceramics) is measured using an electronic microscope (see FIG. 5). In other words, the toughness value K is calculated using the following equation (equation 1).

$$K = 0.018 \left(\frac{E}{H}\right)^{0.5} \left(\frac{P}{C^{1.5}}\right) \quad \text{(Equation 1)}$$

In the equation, K is the toughness value (MPa·m$^{1/2}$), E is Young's modulus (GPa), H is Vickers hardness (Hv=0.1891P(2a)$^2$), c is a half of a crack length (m), and P is an indenter insertion load (N).

Although the toughness value K can also be measured using a Single Edge V-Notch Beam method (SEVNB method), the toughness value K in the embodiment is measured by the IF method.

The toughness value K50 of the second resin 50 may preferably be 1 MPa·m$^{1/2}$ or more, and may particularly preferably be 1.5 MPa·m$^{1/2}$ or more. When Young's modulus E50 is within the above-mentioned range or more, the second resin 50 rarely fractures even when the second resin 50 receives a shock.

When the toughness value K of a resin is increased, there is a tendency that an adhesive strength of the resin lowers. Accordingly, an upper limit of the toughness value K50 is 5 MPa·m$^{1/2}$, for example.

As has been described above, the first resin 40 is an adhesive agent for fixing the lens 21 to the lens barrel 24. Accordingly, lowering of an adhesive strength of the first resin 40 is not preferable. Meanwhile, it is unnecessary for the first resin 40 to have a large toughness vale K like the second resin 50. Accordingly, the toughness value K of the first resin 40 is smaller than the toughness value K of the second resin 50. For example, the toughness value K40 of the first resin 40 may preferably be 0.3 MPa·m$^{1/2}$ or less.

In other words, the toughness value K50 of the second resin 50 is larger than the toughness value K40 of the first resin 40. Particularly, the toughness value K50 of the second resin 50 may preferably be two times or larger than the toughness value K40 of the first resin 40. When the toughness value K50 is equal to or more than the above-mentioned toughness value K40, an adhesive strength of the lens 21 by the first resin 40 is not largely lowered and hence, it is possible to prevent the fracture of the second resin 50.

To acquire a large toughness value K50, the second resin 50 may preferably be a thermo-setting fiber-reinforced resin. The fiber-reinforced resin is a composite material which enhances the strength by mixing fibers such as aramid fibers or carbon fibers in a resin.

The fiber-reinforced resin can acquire an extremely strong toughness value K by arranging long fibers in a specified direction. However, a shock applied to the second resin 50 is not applied from a specified direction, and a volume of the second resin 50 is extremely small. Accordingly, fibers contained in the second resin 50 are short fibers having a largest length 50 μm or less, preferably 10 μm or less. These fibers are uniformly mixed in the resin. An amount of the fibers contained in the second resin 50 is determined by taking into account a balance between a toughness value K50 and an adhesive strength. For example, an amount of the fibers may preferably be 1 wt % or more and 20 wt % or less. The amount of the fibers may particularly preferably be 3 wt % or more and 10 wt % or less.

With respect to fibers contained in the second resin 50, various fibers which are used in known fiber-reinforced resins can be used. However, particularly in an endoscope for medical use, from a viewpoint of biological compatibility, fibers made of an inorganic material and carbon nanofibers are not preferable. On the other hand, organic material fibers or carbon fibers having a diameter of 0.05 μm or more have excellent biological compatibility. Further, the second resin 50 can have light blocking property as described later with the use of carbon fibers and hence, carbon fibers can be preferably used as a material in forming the second resin 50.

The second resin 50 exhibits favorable adhesive property with the first resin 40 and hence, it is preferable to use the same resin for producing the first resin 40 as a base material. In other words, a thermo-setting epoxy resin is most preferable as the first resin 40 and hence, a thermo-setting epoxy resin in which short fibers are distributed is most preferable as the second resin 50.

In the endoscope 10, although the distal end surface 21SA protrudes from the outer surface 24SA, the stepped portion is covered by the second resin 50 and hence, cleaning and the like can be performed easily. Further, the endoscope 10 has high reliability because fixing of the lens 21 is ensured by the first resin 40, and the second resin 50 having a protruding shape rarely fractures.

The second resin 50 is a light blocking resin containing light blocking particles for preventing a flare, and forms the ring-shaped protruding portion which surrounds the distal end surface 21SA of the lens 21. A protruding amount H50 of the protruding portion from the distal end surface 21SA may preferably be 1 μm or more and 100 μm or less. When the protruding amount H50 is less than the above-mentioned range, a sufficient flare preventing effect cannot be obtained. On the other hand, when the protruding amount H150 of the protruding portion exceeds the above-mentioned range, an irradiation range of an illuminate light is narrowed or the second resin 50 is liable to fracture.

When the second resin 50 contains 0.01 wt % or more and 5 wt % or less of light blocking particles, a light blocking performance of the second resin 50 is ensured. The light blocking particles which the second resin 50 contains are made of a material having a lower light transmissivity than the second resin 50. The light blocking particles are organic material particles, metal particles or inorganic material particles. Two or more kinds of particles made of different materials may be used in combination as the light blocking particles. The shape of the light blocking particle may be an arbitrary shape such as a sphere, an elliptical body shape, a plate shape or a needle shape. The shape of the light blocking particle may be a shape obtained by combining two or more kinds of particles having different shapes. Sizes (particle sizes) of the light blocking particles are, for example, 50 nm to 20 μm. The sizes of the light blocking particles may be uniform over the whole second resin 50 or may be ununiform.

As the light blocking particles, at least one of carbon fibers, carbon black and black titanium oxide may be preferably used from a viewpoint of a cost, a light blocking property and dispersion property of the light blocking particles into a resin. As has been described previously, carbon fibers having an effect of increasing a toughness value K are particularly preferable. In other words, the second resin 50 may preferably be a fiber-reinforced resin which contains carbon fibers as the light blocking particles. The second resin 50 may contain carbon fibers in addition to at least one of the carbon black and black titanium oxide.

The first resin 40 may also preferably contain light blocking particles for preventing the reflection of light on the side surface 21SS of the lens 21. The first light blocking particles which the first resin 40 contains may be equal to the second light blocking particles which the second resin 50 contains or may differ from the second light blocking particles which the second resin 50 contains. Since carbon fibers lower an adhesive strength, it is not preferable to use carbon fibers as the light blocking particles. However, if the carbon fiber content of the first resin 40 is 10% or below of the carbon fiber content of the second resin 50, the first resin 40 may contain carbon fibers.

It has been known that the larger a thickness of a region of the thermosetting resin is, the larger a shrinkage of the thermosetting resin at the time of curing is, and hence peeling is liable to occur. With respect to the second resin 50, an inner peripheral portion of the second resin 50 is disposed on a distal end surface 21SA of the lens 21, and an outer peripheral portion of the second resin 50 is disposed on an outer surface 24SA of the lens barrel 24. A thickness of the outer peripheral portion of the second resin 50 is larger than a thickness of the inner peripheral portion of the lens 21 by the protruding amount D of the distal end surface 21SA. Accordingly, there is a concern that the outer peripheral portion of the second resin 50 becomes an initiation point at which peeling occurs.

Accordingly, as shown in FIG. 4, it is preferable that a contact angle θ of the second resin 50 with respect to the outer surface 24SA of the lens barrel 24 is set to 45 degrees or less.

A light absorbing film, for example, a black chromium plating film may preferably be formed on the wall surface 24SS of the lens barrel 24 for prevention of reflection. In the endoscope 10, a light absorbing film may also preferably be formed on the outer surface 24SA of the lens barrel 24.

When the outer surface 24SA is a mirror surface, it is not easy to set the contact angle θ to 45 degrees or less. However, the light absorbing film such as the black chromium plating film has large surface roughness and hence, the contact angle θ of the second resin 50 can be decreased whereby an adhesive strength can be easily enhanced.

In the above-mentioned description, the description has been made by taking the irradiation optical unit 20 as an example. However, it goes without saying that the image pickup optical unit 30 can have the same advantageous effects as the irradiation optical unit 20 by having the same configuration as the irradiation optical unit 20.

Only the image pickup optical unit 30 may have the above-mentioned configuration. In other words, it is sufficient that the optical member (lens) described above is the distal end member of at least one of the illumination optical system and the image pickup optical system. Further, a plurality of irradiation optical units 20 or a plurality of image pickup optical units 30 may be disposed on the distal end portion 11A.

Second Embodiment

Figure 6:
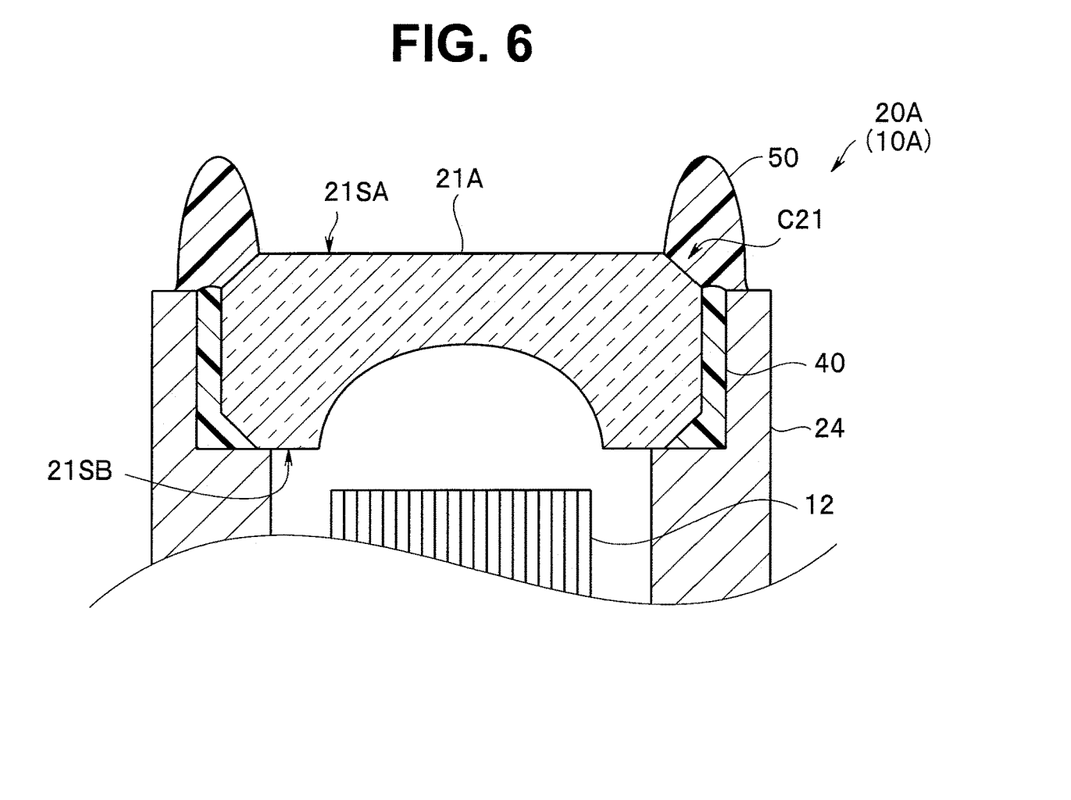
FIG. 6 is a cross-sectional view of an irradiation optical unit of an endoscope of a second embodiment.

An endoscope 10A of the second embodiment is similar to the endoscope 10 and hence, components having the same functions are given with the same symbols, and the description of the components is omitted.

As shown in FIG. 6, in a lens 21A of an optical unit 20A of the endoscope 10A, a cutout C21 is formed on an outer peripheral portion of a distal end surface 21SA. In other words, a ridge line where the distal end surface 21SA of the lens 21 and a side surface 21SS of the lens 21 intersect with each other is chamfered.

Chamfering is not limited to working which cuts out the ridge line in a plane state, but may be so-called round forming working which cuts out the ridge line in a curved surface state. Chamfering also includes molding of the ridge line in substantially the same shape as the case where working is applied to the ridge line. A method for applying working or molding is not limited to a particular method.

In the lens 21A having the cutout C21, chipping rarely occurs on an outer peripheral portion of the distal end surface 21SA even when the lens 21A receives a shock. Note that the lens 21A has a cutout also on a back surface 21SB which faces the distal end surface 21SA.

In the endoscope 10A, a second resin 50 is not disposed in an optical path region of the distal end surface 21SA, and the second resin 50 is disposed only on the cutout C21. In other words, the cutout C21 prevents spreading of the second resin 50 to the optical path region of the distal end surface 21SA. Further, the second resin 50 disposed on the cutout C21 exhibits a higher adhering strength than the case where the second resin 50 is disposed on a flat portion and hence, the endoscope 10A has higher reliability than the endoscope 10.

In the optical unit 20A, the distal end surface 21SA and a center of the side surface 21SS of the lens 21A protrude from an outer surface of a lens barrel by 10 μm or more and 150 μm or less, and a protruding portion of the second resin protrudes from the distal end surface 21SA and the center of the side surface 21SS by 1 μm or more and 100 μm or less.

The endoscope 10A has the advantageous effects of the endoscope 10. Further, in the endoscope 10A, chipping of the lens rarely occurs and, at the same time, the second resin 50 can be easily disposed only on a periphery of the optical path region.

Third Embodiment

Figure 7:
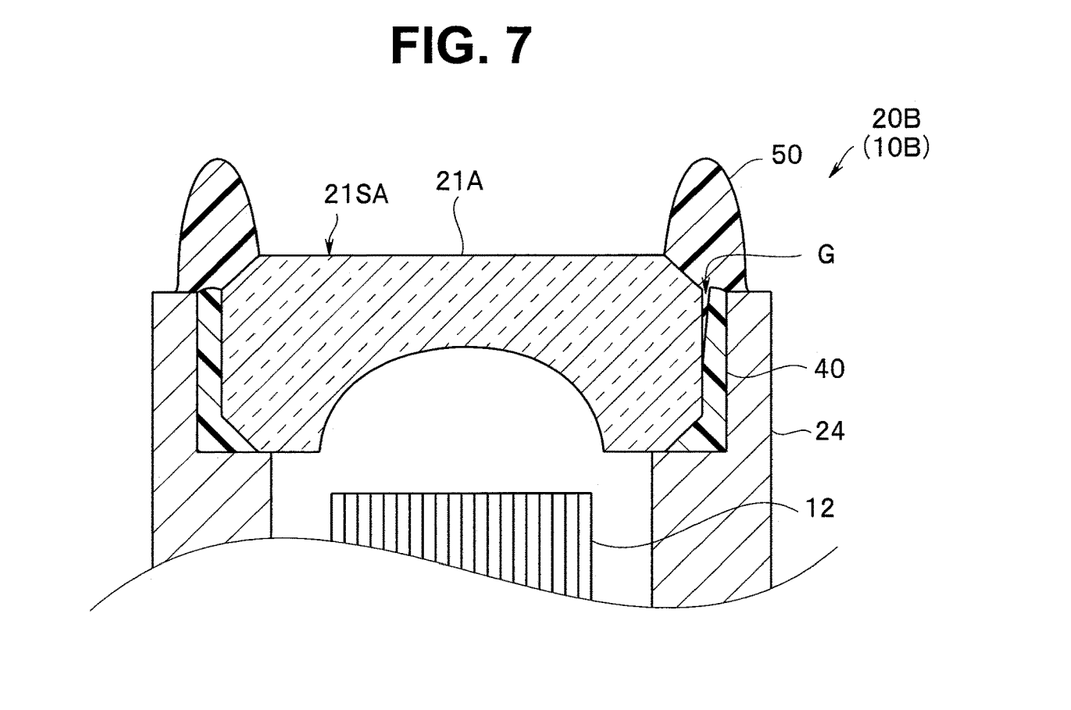
FIG. 7 is a cross-sectional view of an irradiation optical unit of an endoscope of a third embodiment.

An endoscope 10B of the third embodiment is similar to the endoscopes 10 and 10A and hence, components having the same functions are given with the same symbols, and the description of the components is omitted.

As shown in FIG. 7, in an optical unit 20B of the endoscope 10B, a gap G is formed between a first resin 40 and a side surface 21SS of a lens 21. A second resin 50 is also disposed in the gap G.

For example, in the endoscope, there may be a case where the gap G is formed between the first resin 40 and the side surface 21SS of the lens 21 due to deterioration with a lapse of time caused by a shock or the like during the use of the endoscope. In other words, there may be a case where peeling occurs on an adhering surface of the first resin 40 having large Young's modulus. There may also be a case where the second resin 50 which covers the first resin 40 fractures so that a surface of the first resin 40 is exposed. There is also an endoscope in which the second resin 50 is not disposed, as a product specification.

The gap G partially occurs. Even when a width of the gap G is as small as 1 μm, and a depth of the gap G is shallow, the gap G forms a path through which a moisture invades into the endoscope and hence, there is a concern that a reliability of the endoscope is lowered.

The endoscope 10B is prepared by repairing an endoscope in which the gap G occurs due to deterioration with a lapse of time, for example. In other words, in repairing the endoscope, not only a first resin 40 is injected in the gap G but also a second resin 50 which is a ring-shaped protruding portion is disposed. In such a configuration, the second resin 50 is also disposed in the gap G.

Since the second resin 50 is also disposed in the gap G, an adhesive strength is particularly increased by an anchoring effect. The endoscope 10B has higher reliability than not only the endoscopes 10 and 10A but also the endoscope which is repaired by disposing the first resin 40 in the gap G.

The endoscope 10B manufactured by repairing the endoscope in which the second resin 50 is not disposed at the time of manufacturing is newly given with a flare preventing effect.

The gap G in which the second resin 50 is disposed may be formed between the first resin 40 and a wall surface 24SS of a through hole H24. Alternatively, the gap G in which the second resin 50 is disposed may be formed between the first resin 40 and a side surface 21SS of a lens 21 and between the first resin 40 and the wall surface 24SS of the through hole H24 respectively. In other words, the gap G in which the second resin 50 is disposed may be formed in at least either one of a space formed between the first resin 40 and the wall surface 24SS of the through hole H24 and a space formed between the first resin 40 and the side surface 21SS of the lens 21.

The above description is made by taking the irradiation optical units 20, 20A, and 20B as examples. However, it goes without saying that the image pickup optical unit 30 can have the same advantageous effects as the irradiation optical units 20, 20A, and 20B by having the same configurations as the irradiation optical units 20, 20A, and 20B.

Only the image pickup optical unit 30 of the endoscope may have the above-mentioned configuration. In other words, it is sufficient that the optical member (lens) of the endoscope is the distal end member of at least one of the irradiation optical unit 20 and the image pickup optical unit 30. Further, the plurality of irradiation optical units 20 or the plurality of image pickup optical units 30 may be disposed on the distal end portion 11A.

The description has been made by taking flexible endoscopes 10, 10A, and 10B for medical use as examples. However, the endoscopes of the embodiments of the present invention may be endoscopes for industrial use, may be rigid endoscopes, and may be cordless endoscopes having no universal cords.

The present invention is not limited to the above-mentioned embodiments and the like, and various changes, combinations, variations and the like are conceivable without departing from the gist of the present invention.

What is claimed is:

1. An endoscope comprising:
    an insertion section comprising;
        a barrel disposed on a distal end portion of the insertion section and having an opening of a through hole in an outer surface;
        an optical member inserted into the through hole and having a distal end surface which is disposed in a protruding manner from the outer surface;
        a first resin disposed between a wall surface of the through hole and a side surface of the optical member; and
        a second resin disposed on a surface of the first resin, a portion of the barrel disposed around the opening, and an entire circumference of an outer peripheral portion of the distal end surface of the optical member, the second resin having a second fracture toughness value larger than a first fracture toughness value of the first resin.

2. The endoscope according to claim 1, wherein the optical member has a cutout on the outer peripheral portion of the distal end surface, and the second resin is disposed only on the cutout of the optical member, the surface of the first resin and on the portion of the barrel disposed around the opening.

3. The endoscope according to claim 1, wherein the second fracture toughness value of the second resin is two times or larger than the first fracture toughness value of the first resin.

4. The endoscope according to claim 1, wherein the second resin is a fiber-reinforced resin containing one of organic material fibers or carbon fibers.

5. The endoscope according to claim 4, wherein the second resin uses a same thermo-setting resin as the first resin as a base material.

6. The endoscope according to claim 5, wherein the base material is an epoxy resin.

7. The endoscope according to claim 4, wherein the second resin contains fibers having a maximum length of 50 μm or less.

8. The endoscope according to claim 1, wherein further comprising a gap disposed at one or more of:
    between the first resin and the wall surface of the through hole; and
    between the first resin and the side surface of the optical member,
    wherein the second resin is further disposed in the gap.

9. The endoscope according to claim 1, wherein the optical member is a distal end member of at least one of an illumination optical system and an image pickup optical system.

10. The endoscope according to claim 1, wherein the second resin forming a protruding portion which protrudes from the distal end surface of the optical member.

11. The endoscope according to claim 10, wherein
    the distal end surface of the optical member protrudes from the outer surface of the barrel by 10 μm or more and 150 μm or less, and
    the protruding portion of the second resin protrudes from the distal end surface by 1 μm or more and 100 μm or less.

12. The endoscope according to claim 1, wherein the second resin containing light blocking particles.

13. The endoscope according to claim 12, wherein the second resin contains carbon fibers as the light blocking particles.

14. An insertion section of an endoscope comprising:
    a barrel disposed on a distal end portion of the insertion section and having an opening of a through hole in an outer surface;
    an optical member inserted into the through hole and having a distal end surface which is disposed in a protruding manner from the outer surface;
    a first resin disposed between a wall surface of the through hole and a side surface of the optical member; and
    a second resin disposed on a surface of the first resin, a portion of the barrel disposed around the opening, and an entire circumference of an outer peripheral portion of the distal end surface of the optical member, the second resin having a second fracture toughness value larger than a first fracture toughness value of the first resin.

15. The insertion section according to claim 14, wherein the second fracture toughness value of the second resin is two times or larger than the first fracture toughness value of the first resin.

16. The insertion section according to claim 14, wherein the second resin forming a protruding portion which protrudes from the distal end surface of the optical member.

17. The insertion section according to claim 16, wherein
the distal end surface of the optical member protrudes from the outer surface of the barrel by 10 µm or more and 150 µm or less, and
the protruding portion of the second resin protrudes from the distal end surface by 1 µm or more and 100 µm or less.

18. The insertion section according to claim 14, wherein the second resin containing light blocking particles.

19. The insertion section according to claim 18, wherein the second resin contains carbon fibers as the light blocking particles.

20. The insertion section according to claim 14, further comprising a gap disposed at one or more of:
between the first resin and the wall surface of the through hole; and
between the first resin and the side surface of the optical member,
wherein the second resin is further disposed in the gap.

* * * * *